(12) United States Patent
Wonderley

(10) Patent No.: US 11,065,026 B2
(45) Date of Patent: Jul. 20, 2021

(54) DOUBLE EDGED BLADE GRIP ASSEMBLY

(71) Applicant: ACCUTEC, INC., Verona, VA (US)

(72) Inventor: Jeffrey W. Wonderley, Fort Defiance, VA (US)

(73) Assignee: ACCUTEC, INC., Verona, VA (US)

( * ) Notice: Subject to any disclaimer, the term of this patent is extended or adjusted under 35 U.S.C. 154(b) by 0 days.

(21) Appl. No.: 15/812,899

(22) Filed: Nov. 14, 2017

(65) Prior Publication Data

US 2018/0132881 A1 May 17, 2018

Related U.S. Application Data

(60) Provisional application No. 62/421,908, filed on Nov. 14, 2016.

(51) Int. Cl.
| | |
|---|---|
| *A61B 10/02* | (2006.01) |
| *A61B 17/3205* | (2006.01) |
| *B26B 5/00* | (2006.01) |
| *A61B 17/00* | (2006.01) |

(52) U.S. Cl.
CPC ...... *A61B 17/3205* (2013.01); *A61B 10/0266* (2013.01); *B26B 5/006* (2013.01); *A61B 2017/00424* (2013.01)

(58) Field of Classification Search
CPC .. A61B 17/3205; A61B 10/0266; B26B 5/006
See application file for complete search history.

(56) References Cited

U.S. PATENT DOCUMENTS

| | | | |
|---|---|---|---|
| 4,109,380 A | | 8/1978 | Anderson |
| 4,328,615 A | * | 5/1982 | Bowman .................. B26B 29/00 30/32 |
| 4,782,590 A | | 11/1988 | Pope |
| 4,858,323 A | | 8/1989 | Iten |
| 4,943,295 A | | 7/1990 | Hartlaub et al. |
| 5,140,752 A | | 8/1992 | Kasprzak |
| 5,555,892 A | * | 9/1996 | Tipton .................... A61B 10/02 600/564 |
| 5,624,451 A | * | 4/1997 | Segal ............... A61B 17/32093 30/346.5 |
| 5,628,759 A | | 5/1997 | McCool et al. |
| 5,674,234 A | * | 10/1997 | McCool ........... A61B 17/32093 30/32 |
| 5,771,589 A | | 6/1998 | Kim |
| D402,367 S | | 12/1998 | McCool et al. |

(Continued)

FOREIGN PATENT DOCUMENTS

WO    2018148335 A1    8/2018

OTHER PUBLICATIONS

International Search Report and Written Opinion issued in related co-pending International Application No. PCT/US2017/061600, dated Mar. 9, 2018.

(Continued)

*Primary Examiner* — Kenneth E Peterson
*Assistant Examiner* — Liang Dong
(74) *Attorney, Agent, or Firm* — Budzyn IP Law, LLC

(57) ABSTRACT

A double edged blade assembly includes a double edged blade. Additionally, the double edged blade assembly includes two blade grips coupled to the double edged blade. The two blade grips are coupled to the double edged blade at opposite ends of the double edged blade.

15 Claims, 5 Drawing Sheets

(56) References Cited

U.S. PATENT DOCUMENTS

| | | |
|---|---|---|
| D403,035 S | 12/1998 | MacPherson |
| D404,486 S | 1/1999 | McCool et al. |
| D467,387 S | 12/2002 | Wonderley |
| D550,841 S | 9/2007 | Berci et al. |
| D552,795 S | 10/2007 | Wonderley |
| D611,598 S | 3/2010 | Tenger et al. |
| D647,801 S | 11/2011 | Werdowatz |
| D738,501 S | 9/2015 | Renner |
| D778,706 S | 2/2017 | Atkins |
| D807,146 S | 1/2018 | Werdowatz |
| D814,264 S | 4/2018 | Werdowatz |
| 2008/0065126 A1* | 3/2008 | Endo ............... A61B 17/3205 606/167 |
| 2011/0130678 A1* | 6/2011 | Williamson, IV ............... A61B 17/3205 600/564 |
| 2014/0107687 A1* | 4/2014 | Allyn ............... A61B 10/02 606/172 |
| 2016/0051236 A1 | 2/2016 | Allred |
| 2019/0358838 A1 | 11/2019 | Wonderley |

OTHER PUBLICATIONS https://www.pfmmedical.com/en/productcatalogue/kai_biopsyblades/biopsiblade_bb_01/index.html. Date of search, Jun. 15, 2017.
International Search Report & Written Opinion issued in related PCT/US2018/017298; dated Apr. 24, 2018.
INTEGRA; "BioBlade"; Integra Miltex—Medial Device Company Product catalog; 2010.
Extended European Search Report for European Application No. 17869559.9 dated Jun. 3, 2020.

* cited by examiner

DOUBLE EDGED BLADE GRIP ASSEMBLY

CROSS-REFERENCE TO RELATED APPLICATIONS

This application claims benefit and priority to U.S. Provisional Application No. 62/421,908 filed Nov. 14, 2016, the disclosure of which is incorporated by reference herein in its entirety.

BACKGROUND

The present disclosure relates generally to a blade grip assembly for a double edged razor blade.

Certain services, such as dermatological services, rely on a flexibility of razor blades to perform certain procedures. For example, a dermatologist may grip blunt sides of a razor blade between a thumb and an additional gripping finger to flex the razor blade in a manner that limits a cutting surface of the razor blade to provide cutting accuracy. Flexing the razor blade by moving the thumb and the additional gripping finger toward each other results in less of the razor blade in contact with an object being cut. However, such gripping of the razor blade may increase a likelihood of injuries to the dermatologist, or other user, that grips and flexes the razor blade. Further, gripping the blunt sides of the razor blade directly may lead to slippage in a grip applied to the razor blade, which may result in an inaccurate cut.

SUMMARY

The disclosed embodiments provide blade grips and assemblies that include the blade grips. In accordance with an embodiment, a double edged blade assembly includes a double edged blade and two blade grips coupled to the double edged blade. The two blade grips are coupled to the double edged blade at opposite ends of the double edged blade.

In accordance with another illustrative embodiment, a double edged blade grip includes a first curved side that in operation overlays a portion of a double edged blade when coupled to the double edged blade. Additionally, the double edged blade grip includes a second curved side that in operation provides a grip surface during use. The second curved side contains a plurality of teeth extending from a body of the double edged blade grip. Further, the double edged blade grip has at least one boss integrally formed on a coupling side of the double edged blade grip. The at least one boss is deformed plastically to secure the double edged blade grip to the double edged blade.

In accordance with another illustrative embodiment, a blade grip includes a first curved side with a first length and a second curved side with a second length. The first length is longer than the second length. The blade grip also includes a plurality of teeth extending from the second curved side, and the teeth provide a gripping surface. Further, the blade grip includes a coupling side that in operation couples with a blade. Furthermore, the blade grip has at least one boss extending from the coupling side, and the at least one boss in operation engages with the blade to secure the blade grip to the blade.

Additional details of the disclosed embodiments are provided below in the detailed description and corresponding drawings.

BRIEF DESCRIPTION OF THE DRAWINGS

Illustrative embodiments of the present invention are described in detail below with reference to the attached figures, which are incorporated by reference herein, and wherein.

The illustrated figures are only exemplary and are not intended to assert or imply any limitation with regard to the environment; architecture, design, or process in which different embodiments may be implemented.

DETAILED DESCRIPTION

In the following detailed description of several illustrative embodiments, reference is made to the accompanying drawings that form a part hereof, and in which is shown by way of illustration specific embodiments in which the invention may be practiced. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Unless otherwise specified, any use of any form of the terms "connect," "engage," "couple," "attach," or any other term describing an interaction between elements is not meant to limit the interaction to direct interaction between the elements and may also include indirect interaction between the elements described. Further, any use of any form of the terms "connect," "engage," "couple," "attach," or any other term describing an interaction between elements includes items integrally formed together without the aid of extraneous fasteners or joining devices. In the following discussion and in the claims, the terms "including" and "comprising" are used in an open-ended fashion, and thus should be interpreted to mean "including, but not limited to". Unless otherwise indicated, as used throughout this document, "or" does not require mutual exclusivity.

The subject matter disclosed in the present application provides an assembly for securely grasping a razor blade. In specific applications, it is desirable for a user of a razor blade to securely, grasp non-cutting edges of a razor blade to provide a flex on the razor blade during a cutting operation. Accordingly, blade grips installed on the non-cutting edges of the razor blade provide locations to securely grasp the razor blade to provide the flex while minimizing grasp slippage and contact with the cutting edges of the razor blade. By way of example, a dermatologist may use the razor blade assembly disclosed herein to take a sample of tissue during a biopsy procedure.

Figure 1:
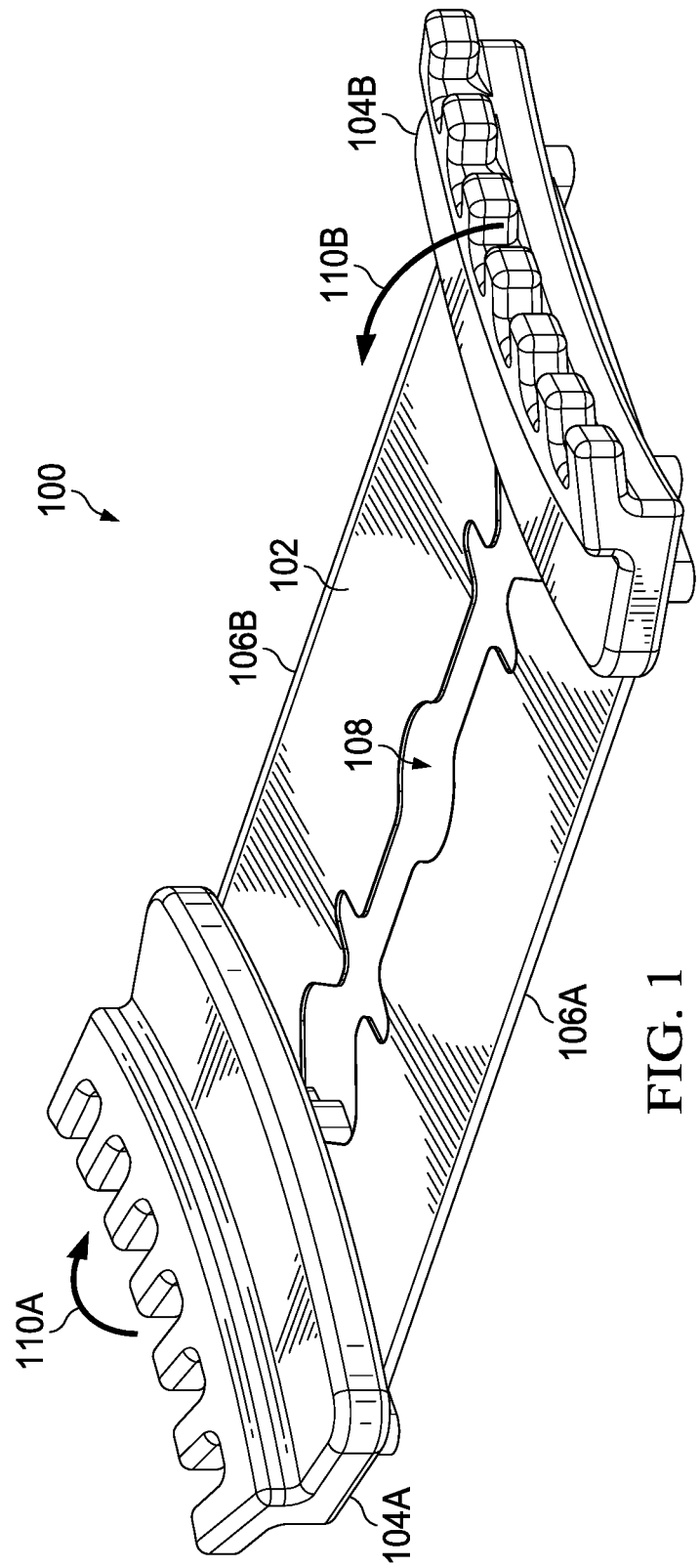
FIG. 1 is a perspective view of a double edged blade assembly, in accordance with an embodiment.

FIG. 1 is a perspective view of a double edged blade assembly 100, in accordance with an embodiment. The double edged blade assembly 100 includes a double edged blade 102 and blade grips 104A and 104B. The blade grips 104A and 104B couple to the double edged blade 102 along surfaces perpendicular to blade edges 106A and 106B. Additionally, the double edged blade 102 may include an opening 108, which is a standard cutout shape for double edged razor blades. It may be appreciated that the shape of the opening 108 may vary. For example, the opening 108 may be limited to portions of the double edged blade 102 that mates with the blade grips 104A and 104B to increase rigidity and robustness of the double edged blade 102. The opening 108 may also increase in size in comparison to the opening 108 depicted in FIG. 1. Increasing the size of the opening 108 may increase flexibility of the double edged blade 102, which may be desirable for cutting materials with heightened levels of precision.

In the illustrated embodiment, a user, such as a dermatologist, is able to grasp the blade grips 104A and 104B with two fingers. The user is then able to flex the double edged blade 102 by applying a force in directions 110A and 110B on the blade grips 104A and 104B, respectively, in such a manner that the blade grips 104A and 104B move toward one another. The force applied on the blade grips 104A and 104B results in the double edged blade 102 flexing into a shallow 'u' shape.

While the double edged blade 102 is flexed, the user applies one of the blade edges 106A or 106B to a surface of an object for cutting. For example, the user may adjust how much pressure is applied on the blade grips 104A and 104B to create a deeper or shallower flex in the double edged blade 102. The deeper flex may provide a small and precise cutting surface on the blade edges 106A or 106B, while the shallower flex may provide a broader cutting surface on the blade edges 106A or 106B.

Figure 2:
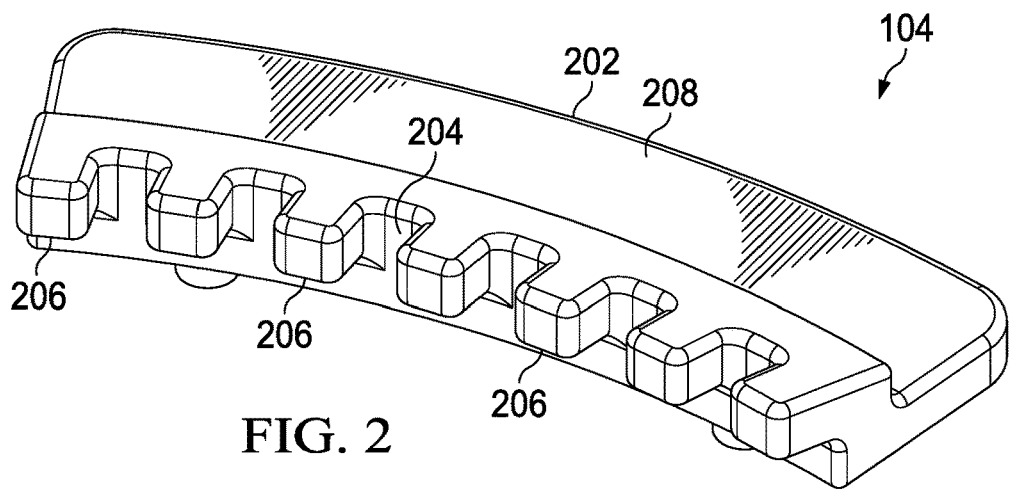
FIG. 2 is a perspective view of a blade grip of the double edged blade assembly of FIG. 1, in accordance with an embodiment.

Turning to FIG. 2, a perspective view of the blade grip 104 of the double edged blade assembly 100 is depicted, in accordance with an embodiment. The illustrated blade grip 104 may be either the blade grip 104A or the blade grip 104B. That is, the blade grips 104A and 104B of FIG. 1 may be formed from the same mold resulting in the blade grips 104A and 104B that are substantially identical. As used herein, the term substantially identical may include minor variations resulting from a manufacturing process. For example, the blade grips 104A and 104B may be made using the same mold. The blade grip 104 may be made from plastic or any other moldable material. Further, in some embodiments, the blade grip 104 is made from any moldable material that is capable of being sterilized.

The blade grip 104 includes a blade side 202 and a grip side 204. When coupled to the double edged blade 102, the blade side 202 of the blade grip 104 is in contact with the double edged blade 102. The grip side 204 of the blade grip 104 includes teeth 206 extending from a body 208 of the blade grip 104. The grip side 204 may curve away from the double edged blade 102, which reduces a likelihood of a user's fingers slipping from the grip side 204 of the blade grip 104. Further, the teeth 206 are integrally formed in the blade grip 104 and break up a surface of the grip side 204 to provide an enhanced gripping surface. For example, the teeth 206 increase friction on the fingers of a user during operation such that slippage of the blade grip 104 is reduced. Additionally, in an embodiment, the grip side 204 both with the teeth 206 and in an embodiment without the teeth 206 may include a rubber coating or an integral rubber portion to provide an enhanced gripping surface. In another embodiment, the entire blade grip 104 is elastomeric to provide the enhanced gripping surface.

Figure 3:
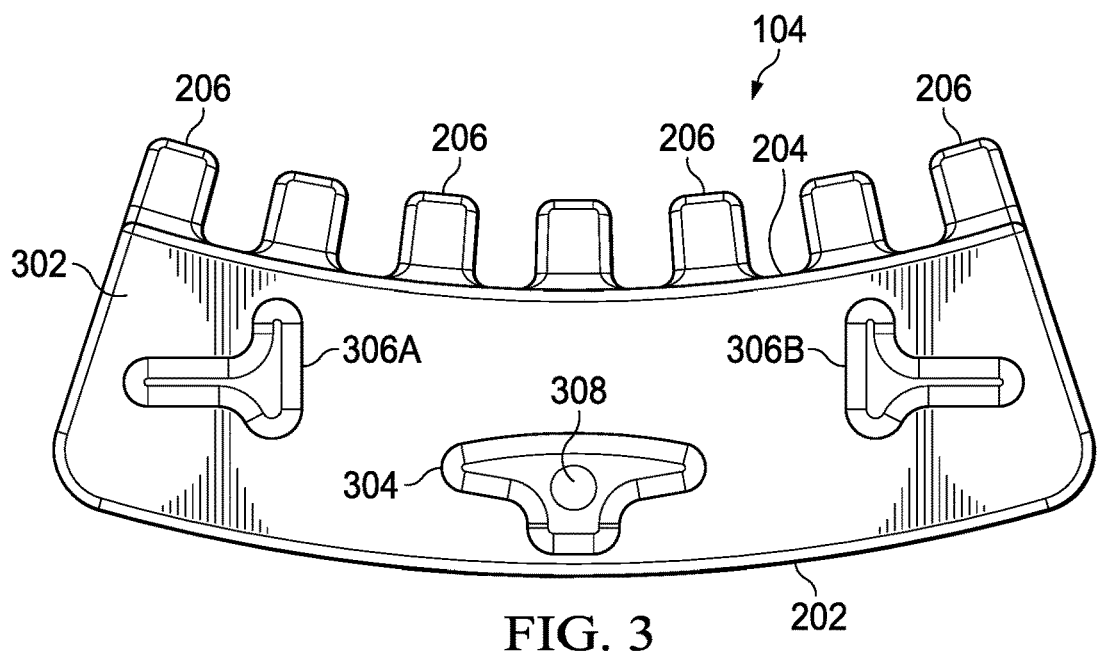
FIG. 3 is a view of a coupling side of the blade grip of the double edged blade assembly of FIG. 1, in accordance with an embodiment.

FIG. 3 is a view of a coupling side 302 of the blade grip 104, in accordance with an embodiment. The coupling side 302 of the blade grip 104 is a portion of the blade grip that interacts with the double edged blade 102 to secure the blade grip 104 to the double edged blade 102. The coupling side 302 includes a central boss 304 and two side bosses 306A and 306B that extend in a direction away from the coupling side 302.

Figure 5:
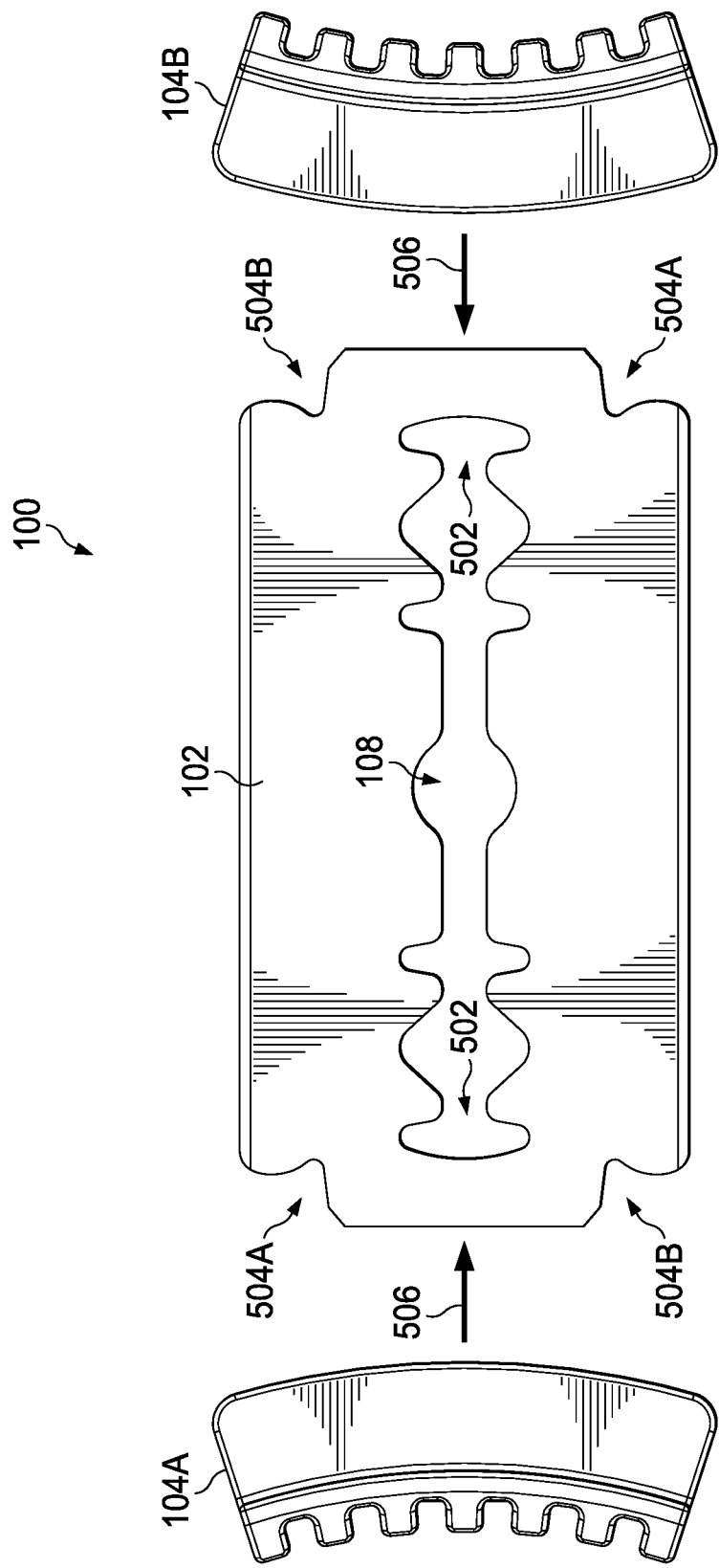
FIG. 5 is an exploded overhead view of the double edged blade assembly of FIG. 1, in accordance with an embodiment.

In an embodiment, the central boss 304 and the side bosses 306A and 306B are shaped to interact with the opening 108 and corner notches 504A and 504B of the double edged blade 102, as illustrated in FIG. 5. For example, the 'T' shape of the central boss 304 is shaped to align with an end portion of the opening 108. Similarly, the side bosses 306A and 306B are shaped to align with the notches 504A and 504B and to run alongside portions of the double edged blade 102.

In an embodiment, the central boss 304 includes a recess 308. The recess 308 may be produced during a molding process of the blade grip 104. For example, when designing plastic components that are formed in molds, it may be desirable to avoid thick areas of plastic whenever possible. The central boss 304, as the largest individual piece protruding from the blade grip 104 benefits from the recess 308 by removing a cross-section of material from the blade grip 104. Removing the cross-section of material may avoid sink effects in the plastic, reduce material usage, and make the blade grip 104 lighter.

While the double edged blade 102 is described herein as a blade with two edges, in some embodiments, the double edged blade 102 may be replaced with a single edged blade. In such embodiments, the blade grips 104A and 104B may remain mostly unchanged with any differences resulting from a change in a shape and a location of the opening 108 and the notches 504A and 504B on the single edged blade. For example, the bosses 304, 306A, and 306B may be reshaped, moved, and/or removed from the coupling side 302 of the blade grips 104 to align with any openings or notches that may be present on the single edged blade.

Figure 4:
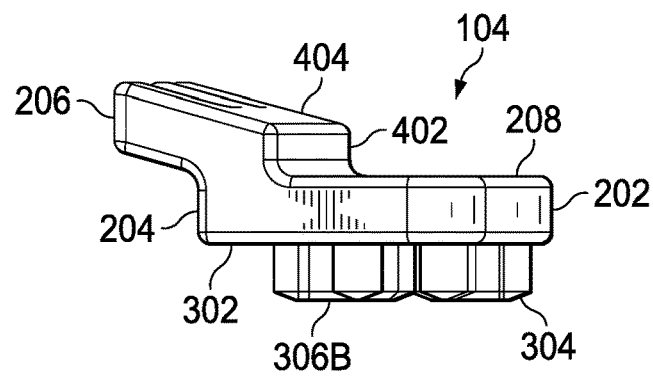
FIG. 4 is a side view of the blade grip of the double edged blade assembly of FIG. 1, in accordance with an embodiment.

FIG. 4 is a side view of the blade grip 104, in accordance with an embodiment. In an embodiment, the teeth 206 include a step 402, which extends away from the body 208 of the blade grip 104. Further, the teeth 206 include an angled surface 404. The angled surface 404 and the step 402 enable gripping of the double edged blade assembly at a position further from a point where the blade grip 104 couples to the double edged blade 102. That is, the step 402 positions the teeth 206 on a different horizontal plane from the body 208 of the blade grip 104. With this positioning, a user may grip the blade grip 104 with increased leverage while flexing the double edged blade 102 when compared to a blade grip with the teeth 206 positioned flush with the body 208 (e.g., without the step 402). Accordingly, user fatigue may be avoided during use of the double edged blade assembly 100 as less force is exerted on the blade grip 104 to achieve a desired flex in the double edged blade 102.

FIG. 5 is an exploded overhead view of the double edged blade assembly 100, in accordance with an embodiment. The double edged blade 102 includes central openings 502 of the opening 108. The central bosses 304 of the blade grips 104A and 104B are shaped to align with the central openings 502. Additionally, the double edged blade 102 includes the notches 504A and 504B. The side bosses 306A and 306B of each of the blade grips 104A and 104B are shaped to align with the notches 504A and 504B of the double edged blade 102. Accordingly, in an embodiment, the blade grips 104A and 104B each include three coupling points (i.e., the central boss 304 and the side bosses 306A and 306B) that function to secure the double edged blade 102 to the blade grips 104A and 104B.

It may be appreciated that the blade grips 104A and 104B may include more or fewer coupling points to secure the blade grips 104A and 104B to the double edged blade 102. For example, the double edged blade 102 may include additional openings at portions of the double edged blade 102 that are in contact with the blade grips 104A and 104B when the double edged blade assembly 100 is assembled. Additionally, the notches 504A and 504B may be removed from the double edged blade 102, and only the central bosses 304 may interact with the double edged blade 102 to secure the double edged blade 102 to the blade grips 104A and 104B. Further, any combination or position of openings and notches of the double edged blade 102 interacting with corresponding bosses of the blade grip 104 is contemplated.

Additionally, while the two blade grips 104A and 104B are depicted in FIG. 5 coupling to the double edged blade 102, a single blade grip 104 may also be coupled to the double edged blade 102. For example, in an embodiment, the blade grip 104A is coupled to the double edged blade 102, and the blade grip 104B is not attached to the double edged blade 102. In such an embodiment, a user interacts directly with the double edged blade 102 on a side opposite the blade grip 104A. Alternatively, a blade grip 104B with a flat (i.e., not concave) grip side may be installed on the double edged blade 102 on the side opposite from the blade grip 104A. In such an embodiment, the teeth 206 and the curvature of the blade grip 104A are only provided on a single side of the double edged blade 102.

Figure 6:
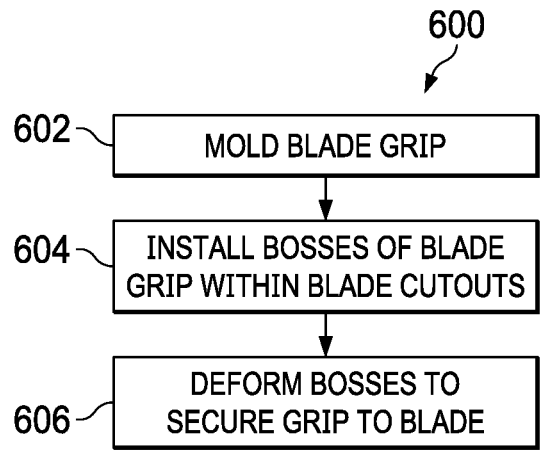
FIG. 6 is a flow chart of method of manufacturing the double edged blade assembly of FIG. 1, in accordance with an embodiment.

Upon completion of a molding process that produces the blade grips 104A and 104B, the blade grips 104A and 104B are installed on the double edged blade 102, as indicated by arrows 506. To help illustrate, FIG. 6 is a flow chart of method 600 of manufacturing the double edged blade assembly 100, in accordance with an embodiment. Initially, the blade grips 104 are molded. Any molding process capable of producing the blade grips 104 is contemplated as within the scope if this disclosure. For example, the blade grips 104 may be formed using injection molding or compression molding techniques.

After the blade grips 104 are molded, the bosses 304, 306A, and 306B are installed within the openings 108 and the notches 504A and 504B of the double edged blade 102. As mentioned above, the bosses 304, 306A, and 306B have a close fit with the openings 108 and the notches 504A and 504B. For example, contact between the bosses 304, 306A, and 306B of the blade grip 104 and the opening 108 and the notches 504A and 504B of the double edged blade 102 may occur as the blade grips 104A and 104B are installed on the double edged blade 102.

The contact between the double edged blade 102 and the blade grips 104A and 104B may provide partial securement of the blade grips 104A and 104B on the double edged blade 102. As used herein, partial securement may refer to the blade grips 104A and 104B maintaining contact with the double edged blade 102 when no external forces are applied to the blade grips 104A and 104B or the double edged blade 102, but, upon applying external forces, the blade grips 104A and 104B and the double edged blade 102 are separable without any deformation of either the blade grips 104A and 104B or the double edged blade 102. The partial securement of the blade grips 104A and 104B and the double edged blade 102 may ensure that sufficient amounts of material from the bosses 304, 306A, and 306B will overlap the double edged blade 102 upon plastically deforming the bosses 304, 306A, and 306B to permanently secure the blade grips 104A and 104B to the double edged blade 102.

At block 606, the bosses 304, 306A, and 306B are plastically deformed to permanently secure the blade grips 104A and 104B to the double edged blade 102. As used herein, permanently securing the blade grips 104A and 104B to the double edged blade 102 may refer to securing the blade grips 104A and 104B to the double edged blade 102 in an irreversible manner. Further, in an embodiment, the term permanent securement may be defined as securement that sufficiently resists separation when the device is operating under an amount of force considered within a normal operating parameter of the device. That is, permanent securement, in some embodiments, means that the blade grips 104A and 104B will not separate from the doubled edged blade 102 when the double edged blade assembly 100 is used during a biopsy procedure.

To deform the bosses 304, 306A, and 306B, a cold staking procedure may be performed on the bosses 304, 306A, and 306B when properly aligned with the double edged blade 102. The cold staking procedure involves applying pressure on the bosses 304, 306A, and 306B at room temperature to compress the bosses 304, 306A, and 306B. When the bosses 304, 306A, and 306B are compressed, the plastic from the bosses 304, 306A, and 306B extends over edges of the corresponding central opening 502 and corner notches 504A and 504B of the double edged blade 102. Extension of the plastic from the bosses 304, 306A, and 306B over the edges of the double edged blade 102 permanently secures the blade grip 104 to the double edged blade 102. Further, the bosses 304, 306A, and 306B may also be deformed with a heat staking process (i.e., applying heat and pressure to the bosses 304, 306A, and 306B) or through an ultrasonic staking process (i.e., controlled melting of the bosses 304, 306A, and 306B using ultrasonic vibrations), or any other plastic deformation process. Further, in place of deforming the bosses 304, 306A, and 306B, the blade grip 104 may be glued to the double edged blade 102 using an adhesive to permanently secure the blade grip 104 to the double edged blade 102.

In another embodiment, each of the blade grips 104 may include two separate pieces that are coupled together on either end of the double edged blade 102. For example, the blade grips 104 may include one piece with the bosses 304, 306A, and 306B and another piece that is positioned on an opposite side of the double edged blade 102 with recesses shaped to receive the bosses 304, 306A, and 306B. In such an embodiment, the two pieces of the blade grips 104 may be attached to each other and to the double edged blade 102 using ultrasonic welding, staking, or gluing.

Figure 7:
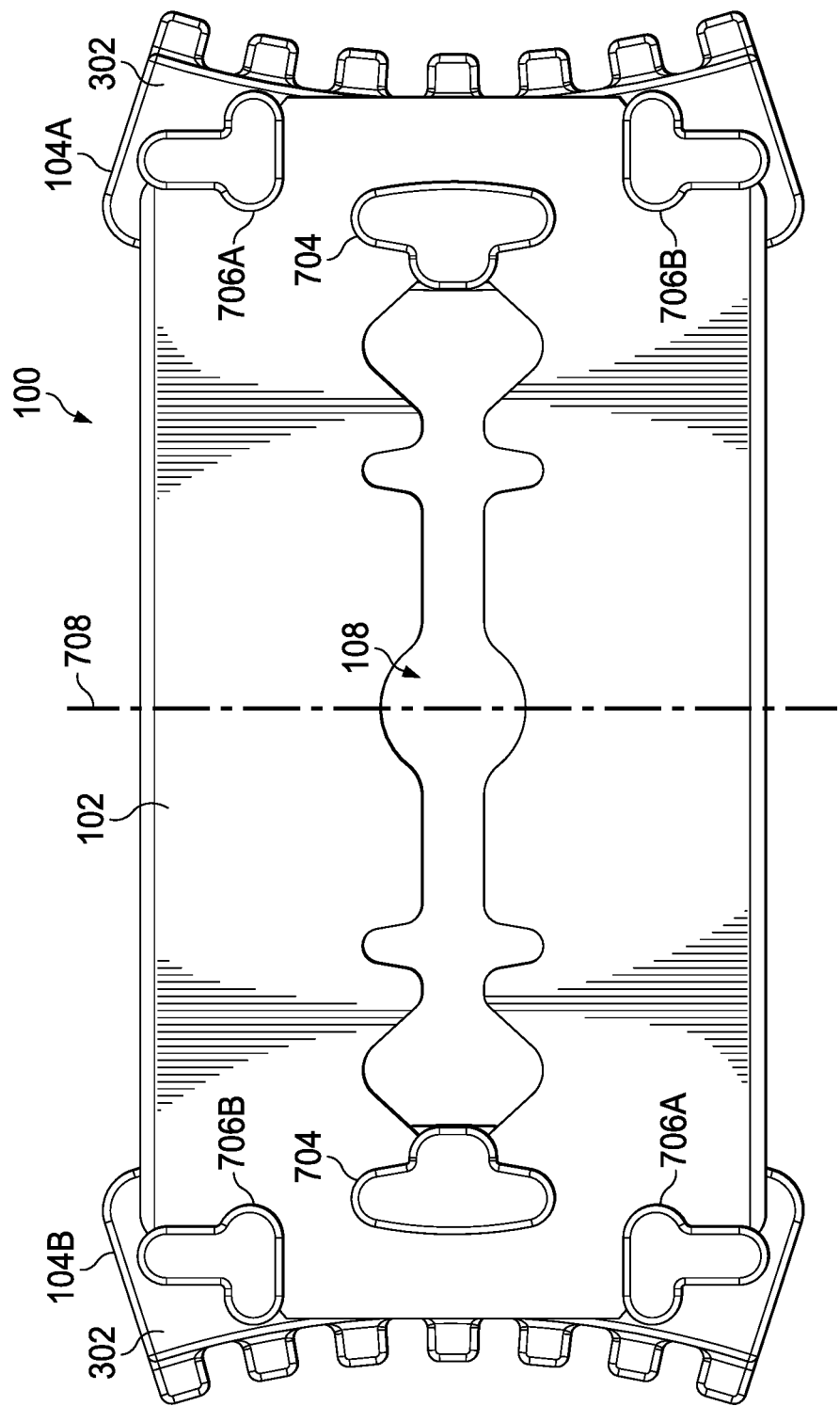
FIG. 7 is an underside view of the double edged blade assembly of FIG. 1, in accordance with an embodiment.

FIG. 7 is an underside view of the double edged blade assembly 100, in accordance with an embodiment. The double edged blade assembly, upon permanent securement of the blade grips 104A and 104B to the double edged blade 102 includes a deformed central boss 704 and deformed side bosses 706A and 706B. As a result of a deformation process, the deformed bosses 704, 706A, and 706B extend over portions of the double edged blade 102 to secure the doubled edged blade 102 to the blade grips 104A and 104B. For example, the deformed bosses 704, 706A, and 706B are flattened when compared to the bosses 304, 306A, and 306B in a manner similar to a rivet after being bucked. Accordingly, as the deformed bosses 704, 706A, and 706B are flattened, the plastic that formed the bosses 304, 306A, and 306B extends over the double edged blade 102. As mentioned above with reference to FIG. 6, the deformed bosses 704, 706A, and 706B may be deformed when partially secured to the double edged blade 102 using a cold staking process, a heat staking process, an ultrasonic staking process, or any other plastic deformation process that is capable of permanently securing the blade grips 104A and 104B to the double edged blade 102.

As illustrated in both FIGS. 3 and 7, the bosses 304, 306A, and 306E and the deformed bosses 704, 706A, and 706B are generally 'T' shaped. However, it may be appreciated that the bosses 304, 306A, and 306B and the deformed bosses 704, 706A, and 706B may take any shape that aligns with the opening 108 and/or the corner notches 504. Further, the central boss 304 and the deformed central boss 704 may include a shape that extends further along the opening 108 to provide additional securement support for the blade grip 104 to the double edged blade 102. For example, as the deformed central boss 704 extends toward a midpoint 708 of the double edged blade 102, the retention capabilities of the deformed central boss 704 increase due to an increase in material overlap of the deformed central boss 704 over the double edged blade 102. Extending the deformed central boss 704 toward the midpoint 708, in an embodiment, may enable removal of the side bosses 306A and 306B, and the resulting deformed side bosses 706A and 706B, while still maintaining a permanent coupling between the blade grips 104A and 104B and the double edged blade 102.

Figure 8:
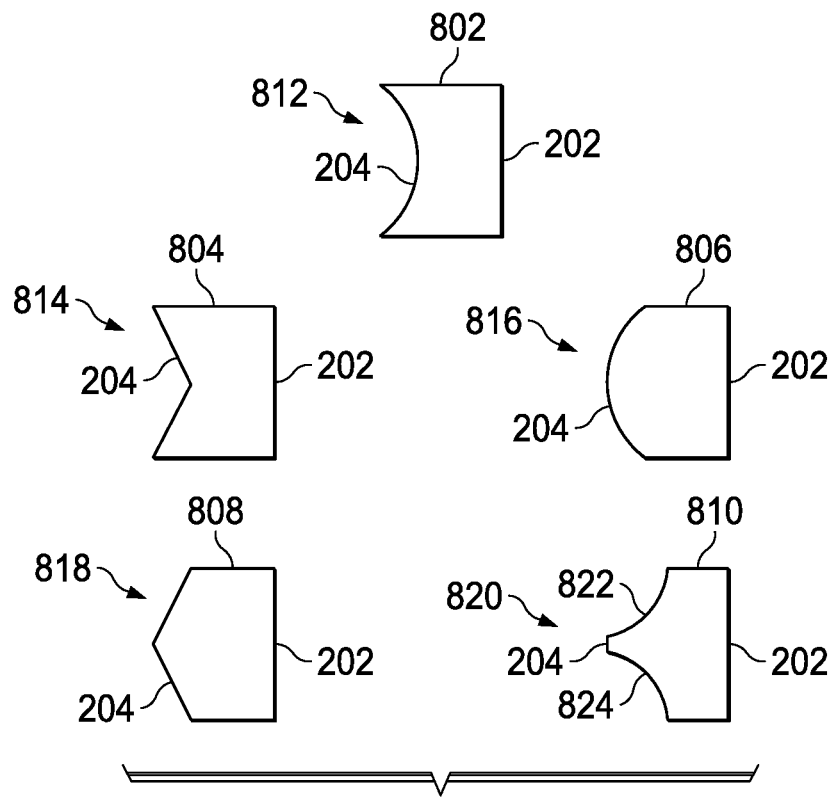
FIG. 8 is a set of varying blade grip configurations of the blade grip of FIG. 2, in accordance with an embodiment.

FIG. 8 is a set of varying blade grip configurations 802, 804, 806, 808, and 810 of the blade grip 104, in accordance with an embodiment. The blade grip configuration 802, for example, includes the blade side 202 and the grip side 204. The grip side 204 of the blade grip configuration 802 has an asymmetrical concave surface 812. In an embodiment, the asymmetrical indentation 812 is designed to provide a different handling feel than the symmetrical curve of the blade grip 104 depicted in FIG. 2.

Additionally, the blade grip configuration 804 includes the grip side 204 with an angled-in surface 814. In other embodiments, the blade grip configuration 806 includes the grip side 204 with a convex surface 816, and the blade grip configuration 808 includes the grip side 204 with an angled-out surface 818. The angled-in surface 814, the convex surface 816, and the angled-out surface 818 each provide different handling feels from each other.

In another embodiment, the blade grip configuration 810 includes the grip side 204 with a double curved surface 820. The double curved surface 820 includes a curve 822 and a curve 824. In an embodiment, the curves 822 and 824 are shaped to receive an index finger and a middle finger of the user to provide an enhanced gripping arrangement over single curve configurations. Further, a blade grip 104 on an opposite side of the double edged blade 102 may also include the blade grip configuration 810, and a thumb of the user may fit within one of the curves 822 or 824. In another embodiment, the blade grip 104 on the opposite side of the double edged blade 102 from the blade grip 104 with the blade grip configuration 810 may be any of the other blade grip configurations 802-808 or the configuration described with reference to FIG. 2. With this in mind, the double edged blade assembly 100 may include any number of combinations of the blade grip configurations when coupling the blade grips 104 to the double edged blade 102. For example, a blade grip 104 with the blade grip configuration 804 may be installed on one side of the double edged blade 102 while a blade grip 104 with the blade grip configuration 806 is installed on an opposite side of the double edged blade 102.

Further, each of the blade grip configurations 802-810 may include teeth 206 that are integrally formed in the blade grip configurations 802-810 and break up a surface of the grip side 204 to provide an enhanced gripping surface. For example, the teeth 206, which are described in detail above with respect to FIG. 2, increase friction on the fingers of a user during operation such that slippage of the blade grip 104 is reduced. Additionally, in an embodiment, the grip side 204 both with the teeth 206 and in an embodiment without the teeth 206 may include a rubber coating or an integral rubber portion to provide an enhanced gripping surface. In another embodiment, the entire blade grip configurations 802-810 are elastomeric to provide the enhanced gripping surface.

While this specification provides specific details related to certain components of the double edged blade assembly 100, it may be appreciated that the list of components is illustrative only and is not intended to be exhaustive or limited to the forms disclosed. Other components of the double edged blade assembly will be apparent to those of ordinary skill in the art without departing from the scope and spirit of the disclosure. Further, the scope of the claims is intended to broadly cover the disclosed components and any such components that are apparent to those of ordinary skill in the art.

The above disclosed embodiments have been presented for purposes of illustration and to enable one of ordinary skill in the art to practice the disclosed embodiments, but is not intended to be exhaustive or limited to the forms disclosed. Many insubstantial modifications and variations will be apparent to those of ordinary skill in the art without departing from the scope and spirit of the disclosure. For instance, although the flow diagram depicts serial processes, some of the steps/blocks may be performed in parallel or out of sequence, or combined into a single step/block. The scope of the claims is intended to broadly cover the disclosed embodiments and any such modification.

It should be apparent from the foregoing disclosure of illustrative embodiments that significant advantages have been provided. The illustrative embodiments are not limited solely to the descriptions and illustrations included herein and are instead capable of various changes and modifications without departing from the spirit of the disclosure.

What is claimed is:

1. A double edged blade assembly, comprising:
   a double edged blade; and
   two separate blade grips, the two blade grips being coupled to the double edged blade at opposite ends of the double edged blade with no direct connection between the two blade grips;
   wherein each blade grip includes a body having a curved grip side with a plurality of teeth and a coupling side interacting with the double edged blade, each of the plurality of teeth extending from a base and terminating at a free end, the coupling side generally lying in a horizontal plane, the base of each of the plurality of teeth being wholly offset from the horizontal plane in a direction opposite the double edged blade, the plurality of teeth each being angled outwardly, away from the horizontal plane, in a direction from the respective base to the respective free end.

2. The assembly of claim 1, wherein the two blade grips are identical.

3. The assembly of claim 1, wherein, for each blade grip, further comprising a step positioned between the body of the blade grip and the plurality of teeth to increase the offset between the free ends of the plurality of teeth and the horizontal plane.

4. The assembly of claim 1, wherein the two blade grips are each coupled to the double edged blade via at least one boss extending from the coupling side of the blade grip and through an opening of the double edged blade.

5. The assembly of claim 4, wherein the at least one boss is plastically deformed to couple the blade grip to the double edged blade.

6. The assembly of claim 4, wherein the at least one boss is integrally formed with the blade grip.

7. The assembly of claim 4, wherein the at least one boss is shaped to align with a shape of the opening of the double edged blade.

8. A double edged blade grip, comprising:
a first curved side configured to overlay a portion of a double edged blade when coupled to the double edged blade;
a second curved side configured to provide a grip surface during use, wherein the second curved side comprises a plurality of teeth extending from a body of the double edged blade grip, each of the plurality of teeth extending from a base and terminating at a free end; and
at least one boss integrally formed on a coupling side of the double edged blade grip, wherein the at least one boss is configured to deform plastically to secure the double edged blade grip to the double edged blade, the coupling side generally lying in a horizontal plane;
wherein the base of each of the plurality of teeth being wholly offset from the horizontal plane in a direction opposite the boss, the plurality of teeth each being angled outwardly, away from the horizontal plane, in a direction from the respective base to the respective free end.

9. The double edged blade grip of claim 8, wherein the plurality of teeth are integrally coupled to the second curved side.

10. The double edged blade grip of claim 8, wherein the at least one boss is configured to align with an existing opening of the double edged blade.

11. The double edged blade grip of claim 8 further comprising a step positioned between the body of the double edged blade grip and the plurality of teeth to increase the offset between the free ends of the plurality of teeth and the horizontal plane.

12. A blade grip, comprising:
a first curved side with a first length;
a second curved side with a second length, wherein the first length is longer than the second length;
a plurality of teeth extending from the second curved side, wherein the teeth provide a gripping surface, each of the teeth extending from a base and terminating at a free end;
a coupling side configured to couple with a blade, the coupling side generally lying in a horizontal plane; and
at least one boss extending from the coupling side, wherein the at least one boss is configured to engage with the blade to secure the blade grip to the blade;
wherein the base of each of the plurality of teeth being wholly offset from the horizontal plane in a direction opposite the boss, the plurality of teeth each being angled outwardly, away from the horizontal plane, in a direction from the respective base to the respective free end.

13. The blade grip of claim 12, wherein the plurality of teeth and the at least one boss are integrally formed with the body of the blade grip.

14. The blade grip of claim 12, wherein the coupling side is configured to couple with the blade using a cold staking process performed on the at least one boss, an ultrasonic welding process performed on the at least one boss, or an adhesive applied to the coupling side, the blade, the at least one boss, or any combination thereof.

15. The blade grip of claim 12 further comprising a step positioned between the body of the blade grip and the plurality of teeth to increase the offset between the free ends of the plurality of teeth and the horizontal plane.

* * * * *